Figure 1:
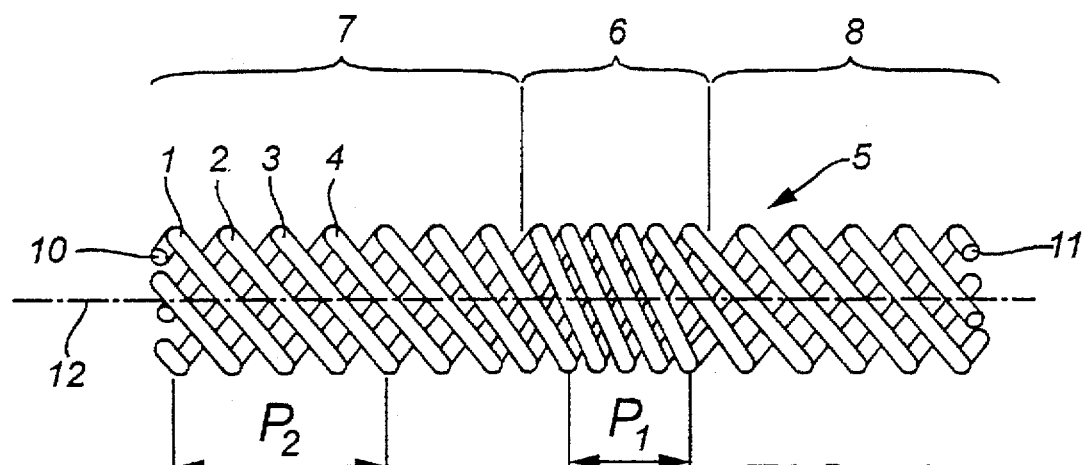

United States Patent [19]

Blanc

[11] Patent Number: 5,749,919
[45] Date of Patent: May 12, 1998

[54] RESILIENT PROSTHESIS FOR WIDENING A CHANNEL, PARTICULARLY A BLOOD VESSEL, AND METHOD FOR MAKING SAME

[75] Inventor: Louis Blanc, Lutry, Switzerland

[73] Assignee: Microfil Industries S.A., Renens, Switzerland

[21] Appl. No.: 513,909
[22] PCT Filed: Dec. 30, 1994
[86] PCT No.: PCT/CH94/00247
   § 371 Date: Sep. 7, 1995
   § 102(e) Date: Sep. 7, 1995
[87] PCT Pub. No.: WO95/18585
   PCT Pub. Date: Jul. 13, 1995

[30] Foreign Application Priority Data

Jan. 10, 1994 [FR] France ................ 94 00302

[51] Int. Cl.[6] ............................ A61F 2/04
[52] U.S. Cl. ............... 623/1; 623/12; 606/194; 606/198
[58] Field of Search ................... 623/1, 11, 12; 600/36; 606/190, 191, 192, 193, 194, 195, 196, 197, 198, 199, 200; 140/92.1

[56] References Cited

U.S. PATENT DOCUMENTS 4,300,244  11/1981  Bokros .
5,171,262  12/1992  MacGregor ..................... 623/1
5,575,818  11/1996  Pinchuk ........................ 623/1

FOREIGN PATENT DOCUMENTS 1 766 921    1/1970  Germany .
WO 83/00997  3/1983  WIPO .

Primary Examiner—David Isabella
Assistant Examiner—John M. Black
Attorney, Agent, or Firm—Davis and Bujold

[57] ABSTRACT

A resilient prosthesis such as a stent for widening a channel in a living body, particularly a stenotic portion of a blood vessel, is disclosed. The prosthesis (5) consists of a number of lengths of resilient thread (1, 2, 3, 4) helically wound in the same direction, which threads are axially inserted between one another in a substantially cylindrical arrangement without intersecting one another. The threads may be separate or joined together at the ends of the prosthesis. The turns of the threads have a shorter pitch $P_1$ in the mid-portion (6) of the prosthesis than in the other portions thereof (7, 8), so that one separate thread cannot be "screwed" between the others. The ends (10, 11) of the threads all lie in the same plane or are axially offset. The prosthesis may be manufactured at low cost and is useful for performing angioplastic, urological or gynaecological treatments, and generally for widening or supporting any channel in the human or animal body.

14 Claims, 3 Drawing Sheets

RESILIENT PROSTHESIS FOR WIDENING A CHANNEL, PARTICULARLY A BLOOD VESSEL, AND METHOD FOR MAKING SAME

This invention concerns an elastic prosthesis for widening a conduit in a living being, in particular a blood vessel, the prosthesis being generally of an elongated and substantially cylindrical shape.

The invention also concerns a method for manufacturing such a prosthesis.

This type of prosthesis is frequently known by the American term "stent" and can be used in particular, but not exclusively, in blood vessels presenting stenosis, the coronary arteries in particular. As the natural internal diameter of the vessel is reduced in the stenosed region, angioplasty is increasingly being used and consists of widening this diameter by means of an inflatable balloon arranged on a catheter, and then of replacing this balloon by a permanent elastic prosthesis whose the rest diameter is larger than that of the vessel, so that the prosthesis presses permanently against the internal wall of the vessel. In order to put the prosthesis in place it is compressed to reduce its diameter and to insert it in the extremity of a tube which is fed to the desired location, then it is pushed out of the tube so as it dilates due to its inherent elasticity.

Publications EP-A-O 183 372 and WO 83/03752 describe prostheses of this type consisting of a trellis of elastic filaments which are plaited or woven together. Furthermore, the deformations and movements during use of the prosthesis create friction between the wires at the points at which they cross and this prevents the use of metal wires provided with special coatings designed to prevent deposits. These prostheses are relatively expensive. A simpler prosthesis, described for example in WO 83/00997, comprises a single wire wound round in a configuration similar to that of a helical spring. In order to put this prosthesis in place, its diameter can be reduced by twisting it and by fixing it thus on an instrument which serves to feed it into the conduit or the vessel to be widened. However, prostheses of this type have proved susceptible to longitudinal movement by snaking due to the constraints placed on them by the vessel, especially in the region where the natural diameter of the vessel is reduced. This phenomenon is produced by the wire sliding longitudinally along its helical trajectory. The main resistance to this movement, apart from the friction on the walls of the vessel which is relatively minimal, comes from the extremity of the wire which tends to attach itself to the wall of the vessel; this resistance is quite low compared with the widening force applied to the vessel in the stenosed region.

The object of this invention is to avoid the disadvantages mentioned above by creating a prosthesis which can be manufactured at little cost and which applies a relatively strong force in the region of the conduit or vessel which has to be widened and which presents a low risk of snaking after it has been implanted.

To this end, an initial aspect of the invention concerns a prosthesis of the type described above, characterised in that it comprises several segments of elastic wire having a configuration of helical spirals where the direction of the spirals is the same for all the segments of wire, and in that outside the zones of extremity of the prosthesis, the segments of wire are intercalated without crossing in order to form the said substantially cylindrical shape.

In this way it is possible to select the number of segments of wire for the prosthesis in order to confer upon it the desired mechanical characteristics and in particular sufficient expansion forces without its design being costly, as all the segments of wire are similar and do not need to be attached to one another. If necessary, each segment of wire may have a free extremity at each extremity of the prosthesis, so that the longitudinal attachment of the prosthesis in the conduit is improved. In other cases the segments of wire may be interlinked at each extremity of the prosthesis, although they may still form several points of attachment at each extremity.

In a particularly advantageous embodiment the spirals of each segment of wire have a shorter spiral pitch in a median section than in the remaining length of the prosthesis. The prosthesis is therefore more rigid in its median section, which corresponds for preference to the region to be widened in the vessel or conduit; that is to say it can apply greater pressure on this region. On the other hand, it is more supple in its terminal sections, situated in the healthy zones of the vessel or conduit and serving in particular to keep the prosthesis in place. Preferably, the spiral pitch in the remaining length should be at least 1.5 times the spiral pitch in the medial section.

In a first embodiment all the wire segments are identical. They may each have two free extremities and not be attached to each other.

At one extremity of the prosthesis, the free extremities of the wire segments may be located in approximately the same transversal plane. In another embodiment, at one extremity of the prosthesis, the free extremities of the wire segments are staggered axially in relation to one another.

Preferably, the number of wire segments constituting the prosthesis is between 4 and 18 inclusive.

In a particular embodiment, the wire segments may be mutually attached at least two at a time at the extremities of the prosthesis. The said wire segments may be attached by welding. On the other hand, at least some of the wire segments may be made from a single continuous wire which is folded or curved through 180° at each extremity of the prosthesis in order to attach respectively two of the said segments.

Another aspect of this invention concerns a method for manufacturing such a prosthesis in which some or, preferably, all the wire segments are formed from a single continuous wire.

A first form of the method comprises the following stages:

means of support comprising a first and a second support with circular periphery are used, these supports being aligned axially facing one another and each having a series of protruding elements distributed along the periphery of the support, and a central mandrel arranged axially between the two series of protruding elements;

the wire is placed on the support means zigzag fashion by an axial zigzag movement between the two series of protruding elements in order to form a assembly of axial and parallel wire segments distributed around the mandrel, the wire being folded successively round at least one protruding element of the first support, then of the second support, then on at least one other protruding element of the first support and so on;

the wire is cut in order to form two adjacent extremities and the said extremities are attached to one another;

the said assembly of wire segments is twisted around the mandrel in order to confer upon each wire segment a permanent configuration of helical spirals, and the means of support is removed from the said assembly which forms the prosthesis.

A second form of the method comprises the following stages:

> support means are used which comprise a first and a second support with circular periphery aligned axially facing one other, each having a series of protruding elements distributed around the support periphery and a central mandrel arranged axially between the two series of protruding elements;
>
> the wire is placed on the support means zigzag fashion by a helical zigzag movement between the two series of protruding elements, or by an axial zigzag movement combined with an alternating movement of rotation of the support means in order to form an assembly of wires parallel and wound in helical spirals round the mandrel, the wire being folded successively round at least one protruding element of the initial support, then of the second support, then round at least another protruding element of the initial support, and so on;
>
> the wire is cut to form two adjacent extremities and the said extremities are attached to one another; and
>
> the support means are removed from the said assembly which forms the prosthesis.

Figure 2:
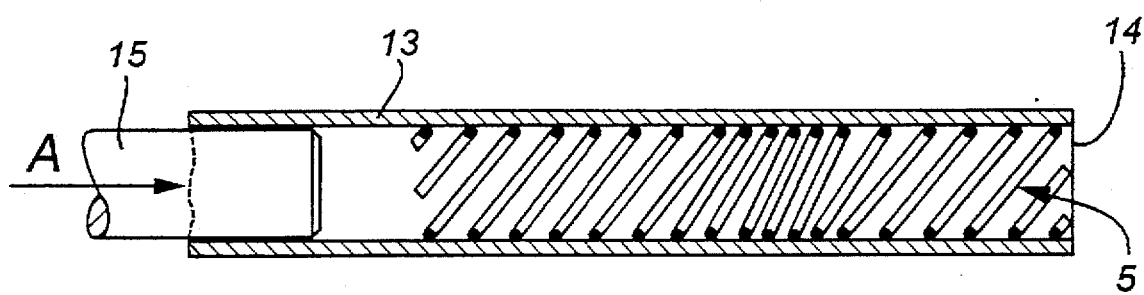
Figure 3:
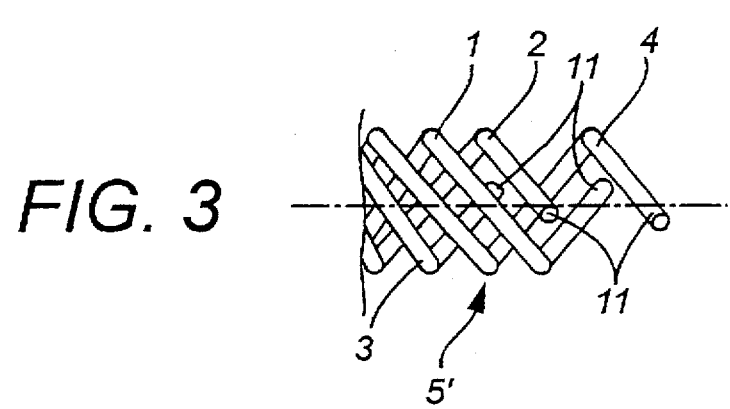
Figure 4:
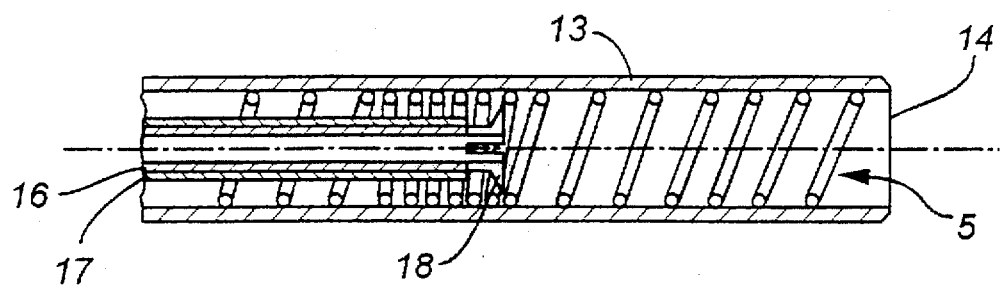
Figure 5:
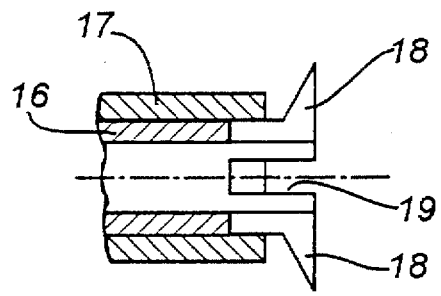
Figure 6:
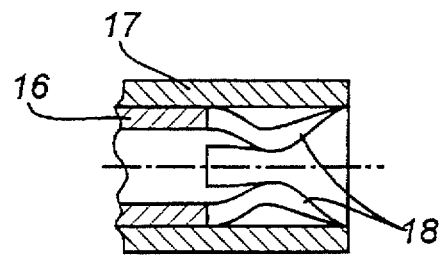
Figure 9:
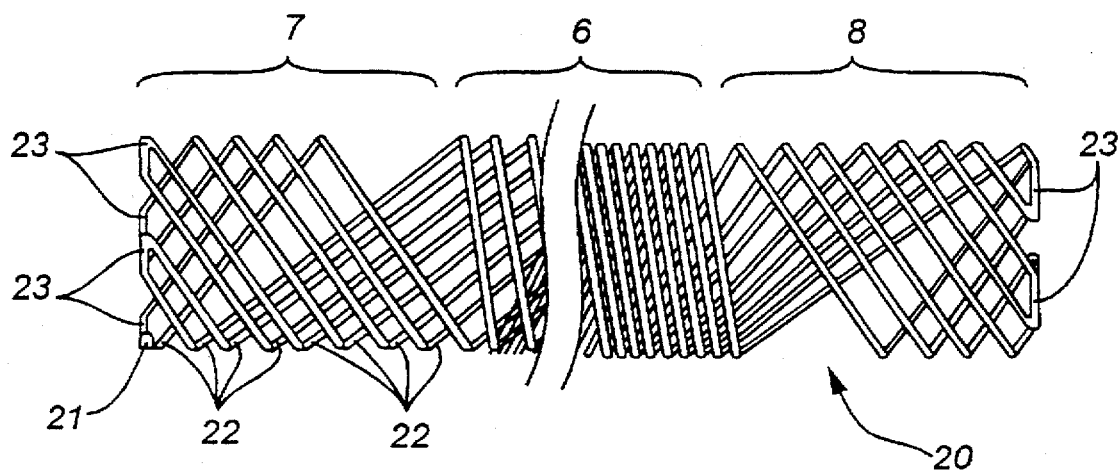
Figure 7:
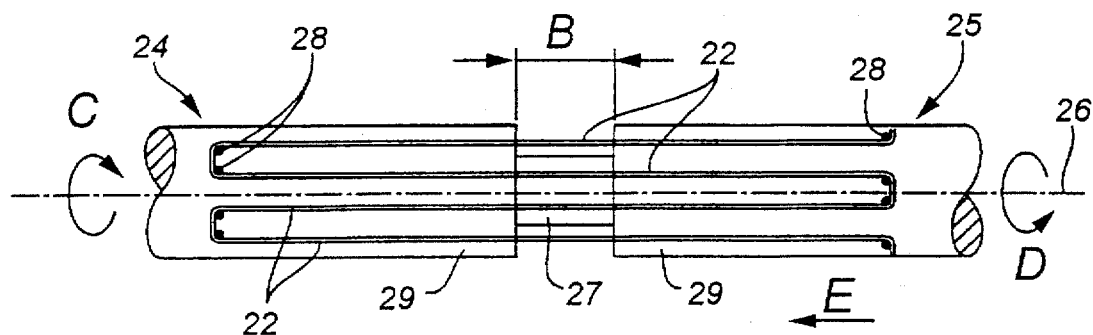
Figure 8:
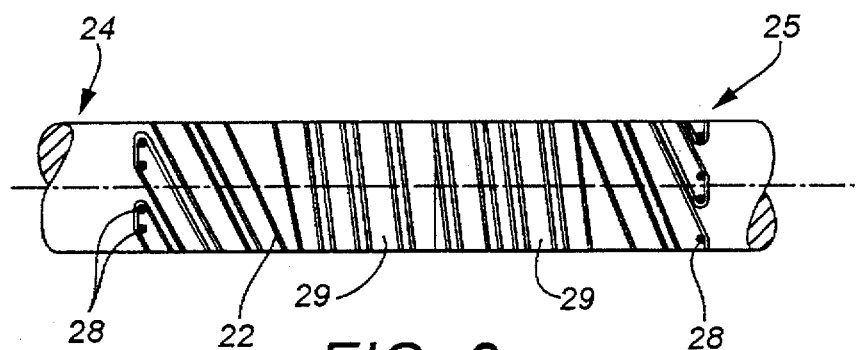
Figure 10:
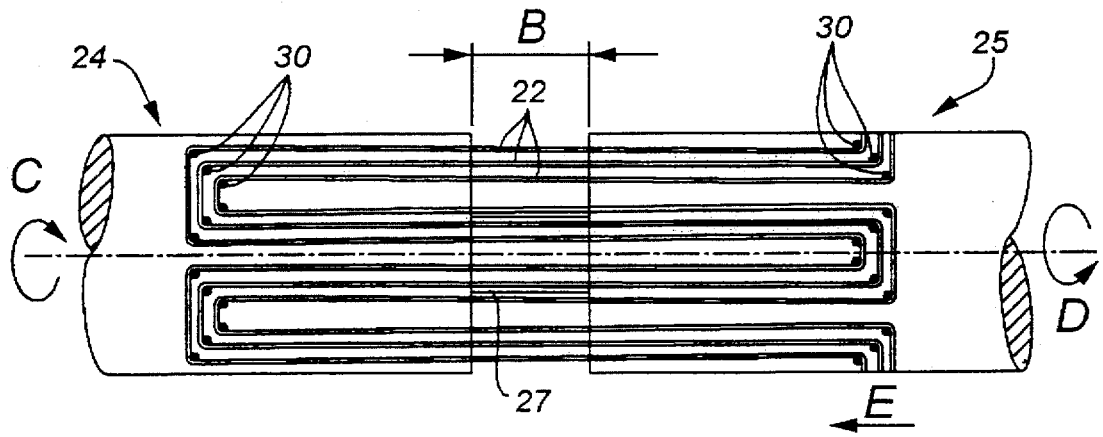

Further features and advantages of the present invention will emerge from the description which follows of example embodiments with reference to the attached drawings in which:

FIG. 1 is a schematic lateral elevation of a first embodiment of a widening prosthesis according to the invention, FIG. 2 is a schematic longitudinal section illustrating the method of implanting the prosthesis shown in FIG. 1, FIG. 3 is a lateral view of an extremity of a widening prosthesis in another embodiment of the invention, FIG. 4 is the same view as FIG. 2, representing another type of implanting device, FIG. 5 shows a detail of FIG. 4 on an enlarged scale, FIG. 6 is the same view as FIG. 5 and represents another position of the device, FIGS. 7 and 8 are lateral views illustrating two successive stages in the method of manufacture of another type of prosthesis according to the invention, FIG. 9 is an enlarged lateral view of the prosthesis thus manufactured, and FIG. 10 is the same view as FIG. 7, illustrating the manufacture of another type of prosthesis according to the invention.

With reference to FIG. 1, four elastic metal wires 1, 2, 3, 4, that is to say four wire segments, together form an elastic prosthesis 5 (or "stent") for widening a blood vessel or another conduit in a living being. The prosthesis is shown in its free or resting state, in which it has a generally cylindrical shape the diameter of which is slightly larger than the natural internal diameter of the vessel concerned. The four wires 1 to 4 are identical to one another; each of them is wound round in helical spirals, although the spiral pitch is not the same along the whole of the length of the prosthesis 5. In a median section 6 to be placed in the region of the vessel to be widened, the spirals have a relatively short pitch $P_1$, slightly larger than four times the width of the wire, so that the they are nearly touching in this region. On the other hand, in two adjacent sections 7 and 8 which form the zones of extremity of the prosthesis 5, the spirals have a pitch $P_2$ greater than $P_1$, so that their axial spacing in relation to one another is greater. The result is that the prosthesis 5 has greater diametrical rigidity in the median section 6 than in the other sections 7 and 8, that is to say that in the vessel where its diameter is reduced by compression, the prosthesis applies greater diametral force in the region of this section 6 where the vessel needs to be specifically widened. Depending on the circumstances, the pitch of the spirals may vary suddenly or progressively between section 6 and each adjacent section 7 and 8, and it may be different in the two sections 7 and 8.

The wires 1, 2, 3, 4 each have two free extremities 10 and 11 which can attach themselves to the internal wall of the vessel in order to prevent longitudinal displacement of the wire and therefore of the whole of the prosthesis 5. In this example the four extremities 10 are in the same transversal plane, and the same applies to the four extremities 11. These extremities may be rounded or cut at an acute angle depending on the circumstances. Of course, the retention effect obtained with the four extremities 10, 11 of the wires at each extremity of the prosthesis is four times greater than with known prostheses made from a single wire.

The wires 1, 2, 3, 4 are not attached to one another. However, they are held one within the other due to the differences in the spiral pitches between sections 6, 7 and 8 of the prosthesis, as this difference largely prevents one wire from being able to move longitudinally and "screwing itself" in between the others. There is in effect a small amount of play between each of the wires in the median section 6, which enables each wire to rotate a fraction of a turn round the longitudinal axis 12 of the prosthesis after which it is stopped by contact with the adjacent wires in the other sections 7 and 8. Here, it is preferable for $P_2$ to be the same as or greater than 1.5 times $P_1$. The same phenomenon occurs if one wire, poorly held by its extremity 10 or 11, has a tendency to creep longitudinally inside the vessel, that is to say the prosthesis 5 offers excellent guarantees of remaining in position throughout a long period of use. On the other hand, it can be removed surgically without difficulty. All that has to be done is withdraw each wire one after the other by seizing each wire using a pincer at one extremity and pulling it by turning, which reduces the diameter of its spirals and enables it to be passed through the interior of the other spirals in order to extract it.

Because all the wires 1 to 4 are identical, the prosthesis 5 can be manufactured very simply by winding the four wires together in parallel on a mandrel of appropriate diameter in order to fashion them. The four wires may be very close to one another during the winding operation, and in the finished prosthesis each group of four wires thus formed may be separated from neighbouring groups by an interval which varies as the spiral pitch varies along the prosthesis. The wires can be therefore be shaped separately and then intercalated. The absence of attachment between the wires considerably facilitates manufacture. Furthermore, if he deems it appropriate, the surgeon can therefore remove a wire before implanting the prosthesis.

FIG. 2 is a schematic view of a device for implanting the widening prosthesis 5 in a vessel. The prosthesis 5 is introduced into a catheter 13 having an extremity with a rounded edge 14 and an internal diameter less than the external diameter of the prosthesis in the resting position, so that the prosthesis 5 is compressed diametrically in the catheter. As all the wires are wound in the same direction, it is easy to twist the prosthesis in order to elastically reduce its diameter in order to place it in the catheter 13. The prosthesis 5 being always of a tubular shape, it can be traversed using another device, for example a guide wire and/or a catheter with an angioplasty balloon. Once the extremity 14 of the catheter has been introduced into the section of vessel to be widened, the prosthesis 5 is pushed out using a mandrel 15 with a cylindrical head which is pushed forward in the direction of the arrow A while the catheter 13 is progressively withdrawn.

It has been shown that the device shown in FIG. 2 only functions properly when the spirals are sufficiently sharply inclined in relation to a radial plane. If not, they tend to jam in the catheter 13. The device shown in FIGS. 4 to 6 enables this disadvantage to be avoided. In this case the mandrel 15 in FIG. 2 is replaced by a push tube 16 arranged so that it slides in an external tube 17. The front extremity of the push tube 16 is shaped to present, for example, four elbowed lugs 18 which, in the position shown in FIGS. 4 and 5, protrude laterally in relation to the external tube 17 and may thus engage between two successive spirals of the prosthesis 5 lodged in the catheter 13. The lugs 18 are flexible and separated by axial notches 19. In the initial position shown in FIG. 5, the external tube 17 prevents them from bending outwards. With this device, once the front extremity of the catheter 13 has crossed the site in a conduit where the prosthesis 5 has to be placed, the catheter 13 starts to be withdrawn whilst maintaining the position of the tubes 16 and 17 in relation to the site, such that the prosthesis 5 is drawn out of the catheter 13 by the lugs 18 and takes up position in the conduit as it is released at the extremity of the catheter 13. Once the prosthesis 5 has left the catheter 13 entirely, the lugs 18 are retracted as shown in FIG. 6 by a relative movement between tubes 16 and 17, then these two tubes are withdrawn inside the catheter 13.

Other methods of implanting a prosthesis according to the invention can be envisaged, for example, using the application device described in publication WO 83/00997, using it not for implanting a single helical wire but several helical wires or segments of helical wire together forming a prosthesis according to the invention.

The prosthesis 5 described above may comprise any number of wires starting with two. In the case of two wires only, the different pitches $P_1$ and $P_2$ therefore enable one wire to be held longitudinally in relation to the other, although the angular play is relatively large. Up to about twenty intercalated wires can be used to form the prosthesis, but too large a number of wires is of little advantage as this involves a relatively large pitch and therefore a relatively long prosthesis with each wire comprising several spirals. On the other hand, the more numerous the wires, the better they are held in place by their extremities. At the moment the optimum number of wires is considered to be of the order of four to eighteen or even twenty four depending on the cases for treatment. Tests have shown that it is possible to manufacture such a prosthesis by successively winding several groups of juxtaposed metal wires.

FIG. 3 shows a variant of embodiment of a prosthesis 5' generally similar to prosthesis 5, but where the wires 1, 2, 3, 4 are not of the same length, such that their respective extremities 11 are staggered in relation to one another in the axial direction of the prosthesis. Thus, they are not all in the same section of the vessel, so much so that they can better attach themselves to the wall of vessel and produce less trauma than if they were all acting in the same location.

Another advantageous aspect of the prostheses 5 and 5' described above can be seen in their great axial and diametral flexibility in the regions of extremity 7 and 8. This means that they press less against the healthy regions of the wall of the vessel and thus reduce a risk of reaction in the vessel tissues. It is also possible to have a longer prosthesis so that the support points (at the extremities) are further from the stenosed region which is the most desirable. These particularly flexible regions 7 and 8 may even be in the bend of a vessel which is not generally possible with conventional prostheses.

Where it is feared that the free extremities 10 and 11 of the wires might traumatise the wall of the vessel or conduit concerned, these extremities can be welded two at a time or three at a time etc., in order to form larger heads at the two extremities of the prosthesis. This connection between the wires does not prevent the diameter of the prosthesis from being reduced by twisting during implantation, as the direction of helical winding is the same for all the wires. The fact that the wires are connected to one another thus avoids the risk of one wire accidentally escaping or accidentally remaining in the conduit if the prosthesis is extracted subsequently.

A further development of the variant described above consists of making several wire segments each one extending from one extremity to the other of the prosthesis using the same continuous wire folded at the said extremities. FIG. 9 represents an example of such a prosthesis made from a single continuous metal wire the two extremities of which have been connected by a junction 21, for example by welding or a crimped sleeve tube. In this case, the continuous wire forms eight wire segments 22, connected two at a time by four folded parts 23 at each extremity of the prosthesis 20. The wire segments 22 are wound in helical spirals which are all in the same direction, never cross one another and which have a shorter spiral pitch in the medial section 6 than in the other sections 7 and 8 of the prosthesis as described with reference to FIG. 1. The folded sections ensure that the prosthesis 20 attaches firmly in the conduit in which it is placed with less risk of trauma than in the case of prosthesis 5. Furthermore, as each wire segment 22 is connected to others there is no risk of a wire moving independently nor of one remaining in the conduit when the prosthesis is removed.

FIGS. 7 and 8 illustrate a method and a device for manufacturing the prosthesis 20 shown in FIG. 9. The device comprises a first cylindrical support 24 and a second cylindrical support 25 which are aligned coaxially along a longitudinal axis 26 and which are connected so that they slide by means of an internal cylindrical tenon 27. Each support 24, 25 has a circular row of four pairs of protruding lugs 28 distributed around the periphery of the support. The two lugs 28 of a pair may of course be replaced by a single protruding element fulfilling the same functions. Between the two rows of lugs 28 the body of each support 24, 25 constitutes a cylindrical mandrel 29 on which the wire rests. In order to manufacture the prosthesis 20, the supports 24, 25 are first placed apart in the position shown in FIG. 7 where a specific axial space B is maintained between the extremities of the supports facing one another. The continuous metal wire is placed zigzag fashion between the respective pairs of lugs 28 of the two supports and the wire folded at a right angle round each lug 28 as shown in FIG. 7 in order to form eight wire segments 22 (only the front wire segments 22 are depicted in FIG. 7) parallel to the axis 26. Once the wire has formed a loop its extremities are cut and connected together by conventional means known to those skilled in the art. The subsequent stage consists of twisting the assembly to confer a helical shape upon the segments 22 by relative rotation of the supports 24 and 25 in the direction of the arrows C and D, whilst at the same time moving the supports axially so that they are closer together following the direction of arrow E. Because the segments are free in the initial space corresponding to B, they wind more rapidly in this region due to friction on the mandrel 29 and this produces a shorter spiral pitch in the medial section 6 of the prosthesis 20. At the end of this twisting stage, in the position shown in FIG. 8, the two supports 24 and 25 abut axially.

The helical shape of the wire segments 22 is maintained due to the screwing action of the wire during twisting. Heat treatment may also be used to create this effect. In order to release the prosthesis from the lugs 28 it is sufficient to rotate relatively the supports 24 and 25 in the opposite direction.

FIG. 10 shows a variant of the device shown in FIGS. 7 and 8 which enables the prosthesis to be manufactured using several wires at the same time, three in this example. Each lug 28 (FIG. 7) is therefore replaced by three lugs 30 aligned in an oblique direction and serving to fold each wire at an angle of 90°. The three wires are placed in parallel, that is to say the wire segments 22 never cross one another between the two rows of lugs 30. If the groups of three lugs 30 are inclined alternately in one direction and in the other as shown in the drawing, the wires do not cross one another in the regions of extremity of the prosthesis either. However, a crossing of the wires in these regions would not necessarily constitute a disadvantage and might be permitted in order to simplify the placing of the wires on the supports 24 and 25. The prosthesis is then twisted in the direction of the arrows C, D and E, as shown in the preceding example.

A variant of the method described above may use the same devices, but in the close position shown in FIG. 8, to place the metal wire directly along the helical trajectories desired of the wire segments 22 due to relative movements between the supports 24 and 25 on the one hand and the device which delivers the wire or wires on the other hand. For example, the said device may be fixed, whereas the supports 24 and 25 together effect helical zigzag movements in opposing directions. At each extremity of the prosthesis a small additional rotating movement passes the wire from one lug 28 or 30 to the next. The arrangement shown in FIG. 8 is thus achieved.

The invention is not restricted to the example embodiments and the applications described above, but includes any modification or variant obvious to the average person skilled in the art. The wires may be of any appropriate cross-section such as round, ellipsoidal, flat, etc. The wires comprising the prosthesis may be made of any material appropriate for the use provided for, in particular metals such as biocompatible non-oxidising alloys, super elastic alloys or "memory" alloys, alloys of titanium, tantalum, niobium, platinum etc., and also synthetic materials with the desired characteristics. The multi-spiral structure without crossing of the prostheses according to the invention has the particular advantage in that metal wires can be used which have a superficial coating specially designed to promote tolerance of the prosthesis in the conduit concerned and/or to prevent the formation of deposits of blood platelets or fat, for example. Because the wire segments do not cross, this delicate coating is not subject to erosion by friction as it is in conventional woven or plaited "stents". In addition to blood vessels the ranges of application for such a prosthesis include various conduits in the human or animal body such as urinary, genital, digestive, pulmonary, nasal, auditory and other tracts.

I claim:

1. An elastic prosthesis, having a median section bound by regions of extremity, for widening a conduit in a living being, in particular a blood vessel, said elastic prosthesis being of a substantially elongated and cylindrical shape, wherein said elastic prothesis (5, 20) comprises a plurality of elastic wire filaments (1, 2, 3, 4, 22) having a helical spiral configuration in which the helical spirals have a direction which is the same for each wire filament except in the regions of extremity of the prosthesis, the wire filaments (1, 2, 3, 4, 22) being intercalated with one another without crossing so as to form the said substantially cylindrical shape.

2. The elastic prosthesis according to claim 1, wherein the helical spiral of each wire filament has a shorter helical pitch ($P_1$) in the median section (6) than in the regions of extremity.

3. The elastic prosthesis according to claim 2, wherein the regions of extremity have a helical pitch (P2) which is at least 1.5 times the helical pitch ($P_1$) in the median section (6).

4. The elastic prosthesis according to claim 1, wherein all the wire filaments (1, 2, 3, 4, 22) are identical in size, length, shape, and helical pitch.

5. The elastic prosthesis according to claim 1, wherein the wire filaments (1, 2, 3, 4, 22) each have two free extremities (10, 11), said two free extremities are not connected to one another.

6. The elastic prosthesis according to claim 5, wherein at each extremity of the prosthesis (5), the free extremities (10, 11) of the wire filaments are substantially in a same transversal plane.

7. The elastic prosthesis according to claim 5, wherein at an extremity of the prosthesis (5), the free extremities (11) of the wire filaments are staggered axially in relation to one another.

8. The elastic prosthesis according to claim 1, wherein the elastic prosthesis comprises a number of wire filaments (1, 2, 3, 4, 22), where the number of wire filaments is between 4 and 18 inclusive.

9. The elastic prosthesis according to claim 1, wherein at the extremity of the prosthesis (20), adjacent wire filaments (22) are connected.

10. The elastic prosthesis according to claim 9, wherein at least some of the wire filaments (22) are connected by welding.

11. The elastic prosthesis according to claim 9, wherein at least some of the wire filaments (22) are formed from a single continuous wire which is folded or bent through 180° at each extremity of the prosthesis in order to connect in each case two of the said wire filaments.

12. An elastic prosthesis, having a median section bound by regions of extremity, for widening a conduit in a living being, in particular a blood vessel, said elastic prosthesis being of a substantially elongated and cylindrical shape, wherein said elastic prosthesis (5, 20) comprises a plurality of elastic wire filaments (1, 2, 3, 4, 22) having a helical spiral configuration in which the helical spirals have a direction which is the same for each wire filament except in the regions of extremity of the prosthesis, the wire filaments (1, 2, 3, 4, 22) being intercalated with one another without crossing so as to form the said substantially cylindrical shape;

the wire filaments (1, 2, 3, 4, 22) each having two free extremities (10, 11), said two free extremities not being connected to one another; and wherein at an extremity of the elastic prosthesis (5'), the free extremities (11) of the wire filaments are staggered axially in relation to one another.

13. A method of manufacturing an elastic prosthesis from a continuous metal wire, the prosthesis (5, 20) having a median section bound by more than one region of extremity, for widening a conduit in a living being, in particular a blood vessel, said elastic prosthesis being of a substantially elongated and cylindrical shape and comprising a plurality of elastic wire filaments (1, 2, 3, 4, 22) having a helical spiral configuration in which the helical spirals have a direction which is the same for each wire filament except in the regions of extremity of the prosthesis, the wire filaments (1, 2, 3, 4, 22) being intercalated with one another without crossing so as to form the said substantially cylindrical shape; adjacent wire filaments (22) in the regions of extremity are connected; at least some of the wire filaments (22) are formed from a single continuous wire which is folded or bent through 180° at each extremity of the prosthesis in order to connect in each case two of the said filaments;

comprising the following steps:

providing a means of support comprising a first and a second support (24, 25) with a circular periphery and axially aligning one facing the other and each having a series of protruding elements (28, 30) distributed along the periphery of the support, and a central mandrel (29) arranged axially between the two series of protruding elements;

placing the wire on the means of support in a zigzag fashion using an axial zigzag movement between the two series of protruding elements (28, 30) in order to form an assembly of axial wire filaments (22) which are parallel and distributed around the mandrel, the wire being folded successively around at least one protruding element of the initial support and then of the second support, then around at least one other protruding element of the initial support and so on;

cutting the wire to form two adjacent extremities, said extremities being fixed one to the other;

twisting said assembly of wire filaments (22) around the mandrel (29) to confer upon each wire filament a permanent helical spiral configuration and removing said assembly which forms the prosthesis (20) from the means of support.

14. A method of manufacturing an elastic prosthesis from a continuous metal wire, the prosthesis having a median section bound by more than one region of extremity, for widening a conduit in a living being, in particular a blood vessel, said elastic prosthesis being of a substantially elongated and cylindrical shape and comprising a plurality of elastic wire filaments (1, 2, 3, 4, 22) having a helical spiral configuration in which the helical spirals have a direction which is the same for each wire filament except in the regions of extremity of the prosthesis, the wire filaments (1, 2, 3, 4, 22) being intercalated with one another without crossing so as to form the said substantially cylindrical shape;

adjacent wire filaments (22) in the regions of extremity are connected;

at least some of the wire filaments (22) are formed from a single continuous wire which is folded or bent through 180° at each extremity of the prosthesis in order to connect in each case two of the said filaments;

comprising the following steps:

providing a supports means comprising a first and a second support (2, 25) with a circular periphery and axially aligning one facing the other and each having a series of protruding elements (28, 30) distributed around the periphery of the support, and a central mandrel (29) arranged axially between the two series of protruding elements;

placing the wire on the means of support in a zigzag fashion using a helical zigzag movement between the two series of protruding elements (28, 30), or by an axial zigzag movement combined with an alternating movement of rotation of the means of support in order to form a parallel assembly of wire filaments wound round in helical spirals around the mandrel, the wire being folded successively round at least one protruding element of the initial support, then of the second support, then round at least one protruding element of the initial support and so on;

cutting the wire to form two adjacent extremities, said extremities being fixed one to the other; and removing said assembly which forms the prosthesis (20) from the means of support.

* * * * *